United States Patent [19]
Elsberg et al.

[11] Patent Number: 6,022,432
[45] Date of Patent: Feb. 8, 2000

[54] METHOD OF MAKING PREFASTENED DISPOSABLE ABSORBENT ARTICLES

[75] Inventors: Laura Linda Elsberg; Jennifer Elizabeth Pozniak, both of Appleton, Wis.

[73] Assignee: Kimberly-Clark Worldwide, Inc., Neenah, Wis.

[21] Appl. No.: 09/100,911

[22] Filed: Jun. 19, 1998

[51] Int. Cl.[7] .................................................. B32B 31/00
[52] U.S. Cl. ........................ 156/73.1; 156/227; 156/264; 156/269
[58] Field of Search .................................. 156/73.1, 196, 156/227, 250, 256, 264, 269; 264/442, 443, 444

[56] References Cited

U.S. PATENT DOCUMENTS

| | | | |
|---|---|---|---|
| H1558 | 7/1996 | Goulait et al. | 156/210 |
| H1674 | 8/1997 | Ames et al. | 604/389 |
| D. 290,780 | 7/1987 | Wistrand | D2/10 |

(List continued on next page.)

FOREIGN PATENT DOCUMENTS

| | | | |
|---|---|---|---|
| 667899 | 4/1996 | Australia | A61F 13/56 |
| 2096672 | 11/1993 | Canada . | |
| 2103992 A1 | 2/1994 | Canada | A61F 13/64 |
| 2187021 A1 | 10/1995 | Canada | A61F 13/56 |
| 2187366 A1 | 10/1995 | Canada | A61F 13/56 |
| 0 206 208 B1 | 12/1986 | European Pat. Off. | A61F 13/15 |
| 0 217 032 A2 | 4/1987 | European Pat. Off. | D04H 13/00 |
| 0 251 251 A3 | 1/1988 | European Pat. Off. . | |
| 0 463 276 a1 | 1/1992 | European Pat. Off. | A61F 13/62 |
| 0 532 034 A2 | 3/1993 | European Pat. Off. | A61F 13/15 |
| 0 544 703 B1 | 6/1993 | European Pat. Off. | A61F 13/56 |
| 0 696 911 B1 | 2/1996 | European Pat. Off. | A61F 13/66 |
| 0 753 292 A2 | 1/1997 | European Pat. Off. | A61F 13/15 |
| 0 487 758 B1 | 3/1997 | European Pat. Off. . | |
| 0 809 992 A1 | 12/1997 | European Pat. Off. | A61F 13/62 |
| 0 878 180 A2 | 11/1998 | European Pat. Off. | A61F 13/15 |

(List continued on next page.)

OTHER PUBLICATIONS

Derwent World Patent Database abstract of FR 2762507 A1: Description of RAHALA, "Baby's Disposable Nappy".
Derwent World Patent Database abstract of JP 6–063076 A: Description of Kao Corp. (Kaos), "Throw Away Diaper Or Nappy".
Derwent World Patent Database abstract of JP 95–044941 B2: Description of ZUIKO KK (ZUIK–N), "Simple Solid Diaper For Eliminating Waste of Material by Using Square Shape".
Derwent World Patent Database abstract of JP 9–276334 A: Description of Kao Corp (Kaos), "Disposable Baby Nappy".
Derwent World Patent Database abstract of JP 11–070143 A: Description of TOYO EISAI KK (TOEI–N), "Disposable Diaper For Adults And Children".
Derwent World Patent Database abstract of JP 11–076299 A: Description of UNI–CHARM KK (UNIC–N), "Disposable Diaper".

*Primary Examiner*—James Sells
*Attorney, Agent, or Firm*—Jeffrey B. Curtin

[57] ABSTRACT

A method of making a prefastened disposable absorbent article includes forming a continuous web of interconnected absorbent articles each of which includes a pair of primary fasteners which are located on the side edges of the article in one of the waist regions of the article. The method also includes cutting the continuous web of interconnected articles into discrete absorbent articles which are folded about a fold line extending in a lateral direction through the crotch region of the article thereby positioning the waist regions of the article in a facing relationship. The waist regions are then releasably bonded together. The method further includes folding the primary fasteners over and onto the opposite waist region to releasably engage the opposite waist region to provide the prefastened absorbent article. The releasable bonding step releasably bonds the waist regions together to assist in maintaining the prefastened absorbent article in a prefastened condition when it is pulled on or off over the hips of the wearer.

21 Claims, 5 Drawing Sheets

U.S. PATENT DOCUMENTS

| | | | |
|---|---|---|---|
| D. 389,320 | 1/1998 | Vinnage et al. | D5/63 |
| 1,079,479 | 11/1913 | Earnshaw | 604/392 |
| 1,485,001 | 2/1924 | Wills | 604/392 |
| 1,657,909 | 1/1928 | Abramovich | 604/392 |
| 1,705,194 | 3/1929 | Marinsky | 604/400 |
| 1,762,468 | 6/1930 | Brewer | 604/397 |
| 1,963,334 | 6/1934 | Neilson | 2/237 |
| 2,201,255 | 5/1940 | Wilson, Jr. | 128/284 |
| 2,242,977 | 5/1941 | Marcos | 128/284 |
| 2,475,175 | 7/1949 | Cadous | 2/237 |
| 2,477,914 | 8/1949 | Webb | 128/284 |
| 2,545,761 | 3/1951 | Brink | 128/287 |
| 2,570,963 | 10/1951 | Mesmer | 128/284 |
| 2,630,120 | 3/1953 | Nielson | 128/287 |
| 2,743,725 | 5/1956 | Matthews | 128/284 |
| 2,801,632 | 8/1957 | Burner et al. | 128/284 |
| 2,808,831 | 10/1957 | Winslett | 128/284 |
| 2,830,589 | 4/1958 | Doner | 128/284 |
| 2,833,282 | 5/1958 | Moore | 128/284 |
| 2,910,982 | 11/1959 | Woodward | 128/284 |
| 2,931,361 | 4/1960 | Sostrin | 128/284 |
| 3,039,466 | 6/1962 | Wilson | 128/287 |
| 3,077,193 | 2/1963 | Mann | 128/284 |
| 3,610,244 | 10/1971 | Jones, Sr. | 128/287 |
| 3,638,651 | 2/1972 | Torr | 128/284 |
| 3,653,381 | 4/1972 | Warnken | 128/284 |
| 3,825,006 | 7/1974 | Ralph | 128/287 |
| 3,882,871 | 5/1975 | Taniguchi | 128/287 |
| 4,024,867 | 5/1977 | Mesek | 128/287 |
| 4,051,853 | 10/1977 | Egan, Jr. | 128/287 |
| 4,051,854 | 10/1977 | Aaron | 128/284 |
| 4,066,081 | 1/1978 | Schaar | 128/287 |
| 4,074,716 | 2/1978 | Schaar | 128/287 |
| 4,089,068 | 5/1978 | Swallow | 2/76 |
| 4,090,516 | 5/1978 | Schaar | 128/287 |
| 4,205,679 | 6/1980 | Repke et al. | 128/287 |
| 4,210,143 | 7/1980 | De Jonckheere | 128/287 |
| 4,337,771 | 7/1982 | Pieniak et al. | 128/287 |
| 4,410,327 | 10/1983 | Baggaley | 604/391 |
| 4,500,316 | 2/1985 | Damico | 604/389 |
| 4,515,595 | 5/1985 | Kievit et al. | 604/385 A |
| 4,522,853 | 6/1985 | Szonn et al. | 428/40 |
| 4,525,407 | 6/1985 | Ness | 428/138 |
| 4,563,185 | 1/1986 | Reiter | 604/385 A |
| 4,568,341 | 2/1986 | Mitchell et al. | 604/368 |
| 4,581,772 | 4/1986 | Smith | 2/111 |
| 4,596,055 | 6/1986 | Aach et al. | 2/237 |
| 4,598,528 | 7/1986 | McFarland et al. | 53/430 |
| 4,604,096 | 8/1986 | Dean et al. | 604/385 A |
| 4,610,680 | 9/1986 | LaFleur | 604/385 A |
| 4,610,681 | 9/1986 | Strohbeen et al. | 604/396 |
| 4,615,695 | 10/1986 | Cooper | 604/385 A |
| 4,617,022 | 10/1986 | Pigneul et al. | 604/391 |
| 4,619,649 | 10/1986 | Roberts | 604/396 |
| 4,623,339 | 11/1986 | Ciraldo et al. | 604/359 |
| 4,630,320 | 12/1986 | Van Gompel | 2/406 |
| 4,663,220 | 5/1987 | Wisneski et al. | 428/221 |
| 4,675,918 | 6/1987 | O'Brien | 2/402 |
| 4,699,622 | 10/1987 | Toussant et al. | 604/389 |
| 4,704,116 | 11/1987 | Enloe | 604/385 A |
| 4,726,874 | 2/1988 | Van Vliet | 156/495 |
| 4,728,326 | 3/1988 | Gilles | 604/391 |
| 4,743,239 | 5/1988 | Cole | 604/385 R |
| 4,747,846 | 5/1988 | Boland et al. | 604/38 A |
| 4,753,646 | 6/1988 | Enloe | 604/385 R |
| 4,753,650 | 6/1988 | Williams | 604/389 |
| 4,798,603 | 1/1989 | Meyer et al. | 604/378 |
| 4,801,485 | 1/1989 | Sallee et al. | 428/198 |
| 4,808,252 | 2/1989 | Lash | 156/73.1 |
| 4,826,499 | 5/1989 | Ahr | 604/389 |
| 4,850,988 | 7/1989 | Aledo et al. | 604/385.1 |
| 4,850,992 | 7/1989 | Amaral et al. | 604/389 |
| 4,857,067 | 8/1989 | Wood et al. | 604/389 |
| 4,883,481 | 11/1989 | Blanchard | 604/385.1 |
| 4,892,598 | 1/1990 | Stevens et al. | 156/91 |
| 4,904,252 | 2/1990 | Fitzgerald | 604/385.1 |
| 4,909,802 | 3/1990 | Ahr et al. | 604/385.1 |
| 4,911,702 | 3/1990 | O'Leary et al. | 604/389 |
| 4,917,682 | 4/1990 | Lancaster et al. | 604/385.2 |
| 4,936,840 | 6/1990 | Proxmire | 604/385.2 |
| 4,937,887 | 7/1990 | Schreiner | 2/402 |
| 4,938,753 | 7/1990 | Van Gompel et al. | 604/385.2 |
| 4,944,733 | 7/1990 | Casale | 604/385.1 |
| 4,961,736 | 10/1990 | McCloud | 604/385.1 |
| 4,988,346 | 1/1991 | Pfefferkorn | 604/389 |
| 4,998,929 | 3/1991 | Bjorksund et al. | 604/385.2 |
| 5,019,072 | 5/1991 | Polski | 604/389 |
| 5,019,073 | 5/1991 | Roessler et al. | 604/391 |
| 5,040,244 | 8/1991 | Tubbs | 2/237 |
| 5,062,839 | 11/1991 | Anderson | 604/385.1 |
| 5,066,289 | 11/1991 | Polski | 604/389 |
| 5,069,678 | 12/1991 | Yamamoto et al. | 604/385.1 |
| 5,074,854 | 12/1991 | Davis | 604/385.1 |
| 5,087,253 | 2/1992 | Cooper | 604/385.1 |
| 5,106,382 | 4/1992 | Henry | 604/385.2 |
| 5,106,385 | 4/1992 | Allen et al. | 604/391 |
| 5,110,403 | 5/1992 | Ehllert | 156/580.1 |
| 5,112,326 | 5/1992 | Quadrini | 604/391 |
| 5,135,522 | 8/1992 | Fahrenkrug et al. | 604/385.1 |
| 5,140,757 | 8/1992 | Terada | 34/66 |
| 5,163,932 | 11/1992 | Nomura et al. | 604/385.2 |
| 5,170,505 | 12/1992 | Rohrer | 2/69 |
| 5,176,668 | 1/1993 | Bernardin | 604/368 |
| 5,176,670 | 1/1993 | Roessler et al. | 604/391 |
| 5,176,672 | 1/1993 | Bruemmer et al. | 604/385.1 |
| 5,185,011 | 2/1993 | Strasser | 604/385.1 |
| 5,186,779 | 2/1993 | Tubbs | 156/161 |
| 5,187,817 | 2/1993 | Zolner | 2/400 |
| 5,192,606 | 3/1993 | Proxmire et al. | 428/284 |
| 5,226,992 | 7/1993 | Morman | 156/62.4 |
| 5,242,436 | 9/1993 | Weil et al. | 604/385.2 |
| 5,275,590 | 1/1994 | Huffman et al. | 604/385.2 |
| 5,304,162 | 4/1994 | Kuen | 604/391 |
| 5,340,431 | 8/1994 | Terada | 156/359 |
| 5,358,500 | 10/1994 | Lavon et al. | 604/385.2 |
| 5,368,584 | 11/1994 | Clear et al. | 604/385.2 |
| 5,368,585 | 11/1994 | Dokken | 604/393 |
| 5,370,632 | 12/1994 | Beplate | 604/385.1 |
| 5,370,634 | 12/1994 | Ando et al. | 604/385.1 |
| 5,373,587 | 12/1994 | Sexton | 2/237 |
| 5,374,262 | 12/1994 | Keuhn, Jr. et al. | 604/391 |
| 5,383,872 | 1/1995 | Roessler et al. | 604/391 |
| 5,386,595 | 2/1995 | Kuen et al. | 2/400 |
| 5,397,639 | 3/1995 | Tollini | 428/343 |
| 5,399,219 | 3/1995 | Roessler et al. | 156/259 |
| 5,401,275 | 3/1995 | Flug et al. | 604/391 |
| 5,423,789 | 6/1995 | Kuen | 604/386 |
| 5,445,628 | 8/1995 | Gipson et al. | 604/392 |
| 5,451,219 | 9/1995 | Suzuki et al. | 604/385.2 |
| 5,462,541 | 10/1995 | Bruemmer et al. | 604/391 |
| 5,489,282 | 2/1996 | Zehner et al. | 604/385.1 |
| 5,499,978 | 3/1996 | Buell et al. | 604/385.2 |
| 5,500,063 | 3/1996 | Jessup | 156/85 |
| 5,509,915 | 4/1996 | Hanson et al. | 604/378 |
| 5,527,302 | 6/1996 | Endres et al. | 604/385.1 |
| 5,531,731 | 7/1996 | Brusky | 604/390 |
| 5,531,732 | 7/1996 | Wood | 604/391 |
| 5,537,722 | 7/1996 | Niederhofer et al. | 24/304 |
| 5,540,796 | 7/1996 | Fries | 156/164 |
| 5,545,158 | 8/1996 | Jessup | 604/385.2 |
| 5,545,275 | 8/1996 | Herrin et al. | 156/731 |
| 5,554,146 | 9/1996 | Niederhofer et al. | 604/391 |

| | | | |
|---|---|---|---|
| 5,562,650 | 10/1996 | Everett et al. | 604/378 |
| 5,569,232 | 10/1996 | Roe et al. | 604/385.2 |
| 5,569,234 | 10/1996 | Buell et al. | 604/396 |
| 5,571,586 | 11/1996 | Gobran | 428/41.3 |
| 5,575,784 | 11/1996 | Ames-Ooten et al. | 604/385.1 |
| 5,582,606 | 12/1996 | Bruemmer et al. | 604/385.2 |
| 5,591,152 | 1/1997 | Buell et al. | 604/385.2 |
| 5,593,401 | 1/1997 | Sosalla et al. | 604/385.2 |
| 5,601,546 | 2/1997 | Tanji et al. | 604/385.2 |
| 5,607,416 | 3/1997 | Yamamoto et al. | 604/397 |
| 5,611,789 | 3/1997 | Seth | 604/391 |
| 5,618,366 | 4/1997 | Suekane | 156/73.1 |
| 5,624,420 | 4/1997 | Bridges et al. | 604/365 |
| 5,624,424 | 4/1997 | Saisaka et al. | 604/385.2 |
| 5,624,428 | 4/1997 | Sauer | 604/391 |
| 5,624,429 | 4/1997 | Long et al. | 604/391 |
| 5,626,574 | 5/1997 | Sasaki et al. | 604/385.2 |
| 5,628,738 | 5/1997 | Suekane | 604/385.1 |
| 5,629,063 | 5/1997 | Gobran | 428/40.1 |
| 5,634,916 | 6/1997 | Lavon et al. | 604/385.1 |
| 5,656,111 | 8/1997 | Dilnik et al. | 156/66 |
| 5,662,637 | 9/1997 | Kitaoka et al. | 604/385.2 |
| 5,662,638 | 9/1997 | Johnson et al. | 604/386 |
| 5,665,084 | 9/1997 | Richmond | 604/389 |
| 5,669,897 | 9/1997 | Lavon et al. | 604/385.2 |
| 5,685,874 | 11/1997 | Buell et al. | 604/396 |
| 5,690,626 | 11/1997 | Suzuki et al. | 604/385.2 |
| 5,690,627 | 11/1997 | Clear et al. | 604/385.2 |
| 5,693,038 | 12/1997 | Suzuki et al. | 604/385.2 |
| 5,707,364 | 1/1998 | Coates | 604/391 |
| 5,711,832 | 1/1998 | Glaug et al. | 156/73.1 |
| 5,769,317 | 6/1998 | Justmann | 156/66 |
| 5,772,825 | 6/1998 | Schmitz | 156/164 |
| 5,788,685 | 8/1998 | Ronnberg et al. | 604/385.2 |
| 5,788,797 | 8/1998 | Herrin et al. | 156/73.1 |
| 5,827,259 | 10/1998 | Laux et al. | 604/385.2 |
| 5,827,260 | 10/1998 | Suzuki et al. | 604/385.2 |
| 5,830,206 | 11/1998 | Larsson | 604/390 |
| 5,855,574 | 1/1999 | Kling et al. | 604/392 |
| 5,876,531 | 3/1999 | Jacobs et al. | 156/66 |
| 5,897,545 | 4/1999 | Kline et al. | 604/386 |
| B1 4,315,508 | 11/1988 | Bolick | 604/392 |
| B1 4,964,860 | 1/1994 | Gipson et al. | 604/391 |

FOREIGN PATENT DOCUMENTS

| | | | |
|---|---|---|---|
| 6-77718 O U | 11/1994 | Japan | A61F 13/15 |
| 7-213553 | 8/1995 | Japan . | |
| 7-227407 | 8/1995 | Japan . | |
| 7-255773 | 10/1995 | Japan . | |
| 7-299094 | 11/1995 | Japan . | |
| 8-229072 | 9/1996 | Japan | A61F 13/56 |
| 9-287 O U | 5/1997 | Japan . | |
| 11-47188 | 2/1999 | Japan . | |
| 1 520 740 | 8/1978 | United Kingdom | A41B 13/02 |
| 2 244 422 | 12/1991 | United Kingdom | A61F 13/15 |
| 2 267 024 | 11/1993 | United Kingdom | A61F 13/66 |
| 2 288 314 | 10/1995 | United Kingdom | A61F 13/15 |
| 2 288 315 | 10/1995 | United Kingdom | A61F 13/15 |
| 2 288 316 | 10/1995 | United Kingdom | A61F 13/56 |
| 2 291 783 | 2/1996 | United Kingdom . | |
| 2 294 867 | 5/1996 | United Kingdom | A41B 13/10 |
| 2 297 473 | 6/1996 | United Kingdom | A41B 13/04 |
| WO 83/04163 A1 | 12/1983 | WIPO | A41B 13/02 |
| WO 90/07313 A1 | 7/1990 | WIPO | A61F 13/15 |
| WO 91/04724 A1 | 4/1991 | WIPO | A61F 13/56 |
| WO 91/08725 A1 | 6/1991 | WIPO | A61F 13/15 |
| WO 92/22274 A1 | 12/1992 | WIPO | A61F 13/15 |
| WO 93/09742 A1 | 5/1993 | WIPO | A61F 13/15 |
| WO 94/17768 A1 | 8/1994 | WIPO | A61F 13/58 |
| WO 95/01148 A1 | 1/1995 | WIPO | A61F 13/56 |
| WO 95/02383 A1 | 1/1995 | WIPO | A61F 13/15 |
| WO 95/13772 A1 | 5/1995 | WIPO | A61F 13/15 |
| WO 95/22951 A1 | 8/1995 | WIPO | A61F 13/15 |
| WO 95/27460 A1 | 10/1995 | WIPO . | |
| WO 95/27462 A1 | 10/1995 | WIPO | A61F 13/56 |
| WO 95/29657 A1 | 11/1995 | WIPO | A61F 13/56 |
| WO 96/03101 A1 | 2/1996 | WIPO | A61F 13/62 |
| WO 96/18315 A1 | 6/1996 | WIPO | A41B 1/10 |
| WO 96/32084 A1 | 10/1996 | WIPO | A61F 13/62 |
| WO 97/15260 A1 | 5/1997 | WIPO | A61F 13/15 |
| WO 97/23186 A1 | 7/1997 | WIPO | A61F 13/58 |
| WO 97/25951 A1 | 7/1997 | WIPO | A61F 13/15 |
| WO 97/31605 A1 | 9/1997 | WIPO . | |
| WO 97/32555 A1 | 9/1997 | WIPO . | |
| WO 97/33547 A1 | 9/1997 | WIPO | A61F 13/66 |
| WO 97/46197 A1 | 12/1997 | WIPO | A61F 13/56 |
| WO 98/03140 A1 | 1/1998 | WIPO | A61F 13/62 |
| WO 98/18421 A1 | 5/1998 | WIPO | A61F 13/15 |
| WO 98/56328 A1 | 12/1998 | WIPO . | |
| WO 99/07319 A1 | 2/1999 | WIPO . | |

METHOD OF MAKING PREFASTENED DISPOSABLE ABSORBENT ARTICLES

FIELD OF THE INVENTION

The present invention relates to disposable absorbent articles which are adapted to contain body exudates. More particularly, the present invention relates to methods of making prefastened disposable absorbent articles which have side bonds and adjustable fastening systems to maintain the articles about the waist of the wearer.

BACKGROUND OF THE INVENTION

It is desired that absorbent articles such as diapers, training pants or incontinence garments provide a close, comfortable fit about the wearer and contain body exudates. Moreover, it is desirable that such absorbent articles, after being soiled, can be removed from the wearer in a convenient and clean manner without undesirably soiling the care giver or surrounding area such as the clothes of the wearer. In certain circumstances, it is also desirable that such absorbent articles are capable of being pulled up or down over the hips of the wearer to allow the wearer or caregiver to easily pull the article on and easily remove the article if it has not been soiled. For example, such absorbent articles can assist in the toilet training of children.

Conventional diapers are provided in an unfastened configuration and have typically included a front waist portion and a back waist portion which are releasably connected about the hips of the wearer during use by conventional fasteners such as adhesive tape fasteners or hook and loop type fasteners. For example, the conventional fasteners have typically included a pair of fasteners, such as adhesive tape tabs, located on the outermost corners of the diaper in the back waist region of the diaper and a complimentary fastener, such as a taping panel, located on the outer surface of the outer cover of the diaper in the front waist portion of the diaper. In such a configuration, the diaper has been positioned between the legs of the wearer and the adhesive tape tabs have been releasably attached to the taping panel to secure the back waist portion to the front waist portion of the diaper to secure the diaper about the waist of the wearer. Such conventional diapers are easy to fasten about and remove from the wearer after use without undesirably soiling the care giver. However, conventional diapers are not provided in a prefastened condition and thus are not configured to be pulled up or down over the hips of the wearer when the fasteners are attached.

Several attempts have been made to provide absorbent articles which effectively contain body exudates, are capable of being pulled up or down over the hips of the wearer and provide ease of cleaning and removal after being soiled. For example, some conventional absorbent articles, such as conventional training pants, have included integral side panels which connect the front waist portion to the back waist portion of the absorbent article. The side panels have been made stretchable such that the waist opening of the absorbent article can expand to allow the absorbent article to be pulled up or down over the hips of the wearer if desired. Such side panels have also been designed such that they may be torn to remove the training pant from the wearer after it has been soiled.

However, many of such attempts have not been completely satisfactory. For example, absorbent articles such as training pants have not always been able to achieve a close conforming fit to the wearer while still being able to expand enough to be pulled up and down over the hips of the wearer. Often such training pants fit the waist of the wearer loosely which can undesirably result in leaks. As a result, many of such articles have not contained bodily exudates as effectively as conventional diaper-type articles which can be adjusted to achieve a more conforming fit to the wearer. Moreover, the removal of soiled absorbent articles which have integral side panels, such as conventional training pants, has not always been completely satisfactory. For example, the side panels have been difficult to tear when attempting to remove the article from the waist of the wearer instead of pulling the article down over the hips of the wearer.

Moreover, the methods of making conventional absorbent articles such as conventional training pants have not always been completely satisfactory. For example, at times it has been difficult to control the side panels when attaching them to the side edges of the training pants and such panels have often become skewed or wrinkled during processing. As a result, the seams along which such panels are connected have often been skewed or discontinuous which can reduce the performance and aesthetics of the article.

Accordingly, despite the attempts to develop improved absorbent articles, there remains a need for absorbent articles which can provide the benefits of conventional training pants and conventional diapers. That is, there remains a need for absorbent articles which conform to the wearer to effectively contain bodily exudates, which are capable of being pulled up and down over the hips and buttocks of the wearer without opening, and which are readily secured about and removed from the wearer in a convenient and clean manner. Moreover, there is a need for improved methods of reliably and consistently making such absorbent articles.

SUMMARY OF THE INVENTION

In response to the difficulties and problems discussed above, a new method of making a prefastened disposable absorbent article which has releasable side bonds and an adjustable fastening system has been discovered. In one aspect, the present invention concerns a method of making a prefastened disposable absorbent article which defines an absorbent, a front waist region, a back waist region, a crotch region which extends between and connects the waist regions, a pair of opposed side edges and a pair of opposed waist edges. The method includes forming a continuous web of interconnected absorbent articles each of which includes a pair of primary fasteners which are located on the side edges of the article in one of the waist regions of the article. The continuous web is selectively cut into discrete absorbent articles. Each of the discrete absorbent articles is folded about a fold line extending in a lateral direction through the crotch region thereby positioning the waist regions in a facing relationship. The waist regions are releasably bonded together and the primary fasteners are folded over and onto the opposite waist region to releasably engage the opposite waist region to provide the prefastened absorbent article.

In another aspect, the present invention concerns a method of making a prefastened disposable absorbent article which comprises the steps of:

a) providing a continuously moving web of outer cover material;

b) intermittently connecting an absorbent chassis to the outer cover to provide a continuously moving web of interconnected absorbent articles each of which includes one absorbent chassis;

c) intermittently attaching a pair of primary fasteners to the laterally opposed side edges of the back waist region of each of the interconnected absorbent articles;

d) selectively cutting the continuous web of interconnected absorbent articles into discrete absorbent articles;

e) folding each of the discrete absorbent articles about a fold line extending in a lateral direction through the crotch region of the absorbent article thereby positioning the waist regions of the absorbent article in a facing relationship with the primary fasteners extending laterally outward beyond the side edges of the article;

f) releasably bonding the front waist region to the back waist region; and g) folding the primary fasteners over and onto the front waist region of the article to releasably engage the front waist region to provide the prefastened absorbent article.

The present invention advantageously provides a method of making a prefastened disposable absorbent article which includes the combination of releasable side bonds and an adjustable fastening system for improved fit and performance. In particular, the present invention provides a method of folding and prefastening a disposable absorbent article in a reliable and consistent manner. The absorbent article of the present invention is capable of being reliably pulled up or down over the hips of the wearer to assist in the toilet training of the wearer similar to conventional training pants. Moreover, similar to conventional diapers, the absorbent article of the present invention can advantageously be applied to and removed from the wearer after it has been soiled with relative ease and cleanliness. For example, the releasable side bonds may be broken and the primary fasteners may be disengaged to allow the caregiver to apply or remove the article similar to conventional diapers. The releasable side bonds further prevent the primary fasteners from contacting the skin of the wearer which can undesirably cause redmarking.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

The present invention concerns methods of making prefastened disposable absorbent articles which are configured to closely conform to the body of the wearer to effectively contain body exudates while being capable of being pulled up or down over the hips and buttocks of the wearer. The prefastened disposable absorbent articles can also be easily secured to and removed directly from the waist of the wearer. As such, the prefastened absorbent articles of the present invention can function like a conventional training pant in their prefastened condition or they can be unfastened prior to or during use to function similar to conventional diapers. The disposable absorbent articles are adapted to be worn adjacent to the body of a wearer to absorb and contain various exudates discharged from the body. As used herein, the term "disposable" refers to articles which are intended to be discarded after a limited use and which are not intended to be laundered or otherwise restored for reuse.

The methods of making the disposable absorbent articles of the present invention will be described in terms of a method of making a disposable diaper article which is adapted to be worn by infants about the lower torso. In particular, the methods will be described in terms of a method of making a prefastened disposable absorbent diaper such as that described in U.S. patent application Ser. No. 08/907,585 entitled "A MULTI-FUNCTIONAL FASTENER FOR DISPOSABLE ABSORBENT ARTICLES" and filed Aug. 8, 1997 in the name of J. Suprise, and U.S. Patent Application entitled "DISPOSABLE ABSORBENT ARTICLES HAVING PASSIVE SIDE BONDS AND ADJUSTABLE FASTENING SYSTEMS" filed on the same date as the present application in the name of Elsberg and having Attorney Docket No.13,611, the disclosures of which are hereby incorporated by reference. It is understood that the methods of the present invention are equally adaptable for use in making other types of absorbent articles such as adult incontinent products, training pants, feminine hygiene products, other personal care or health care garments, and the like.

Figure 1:
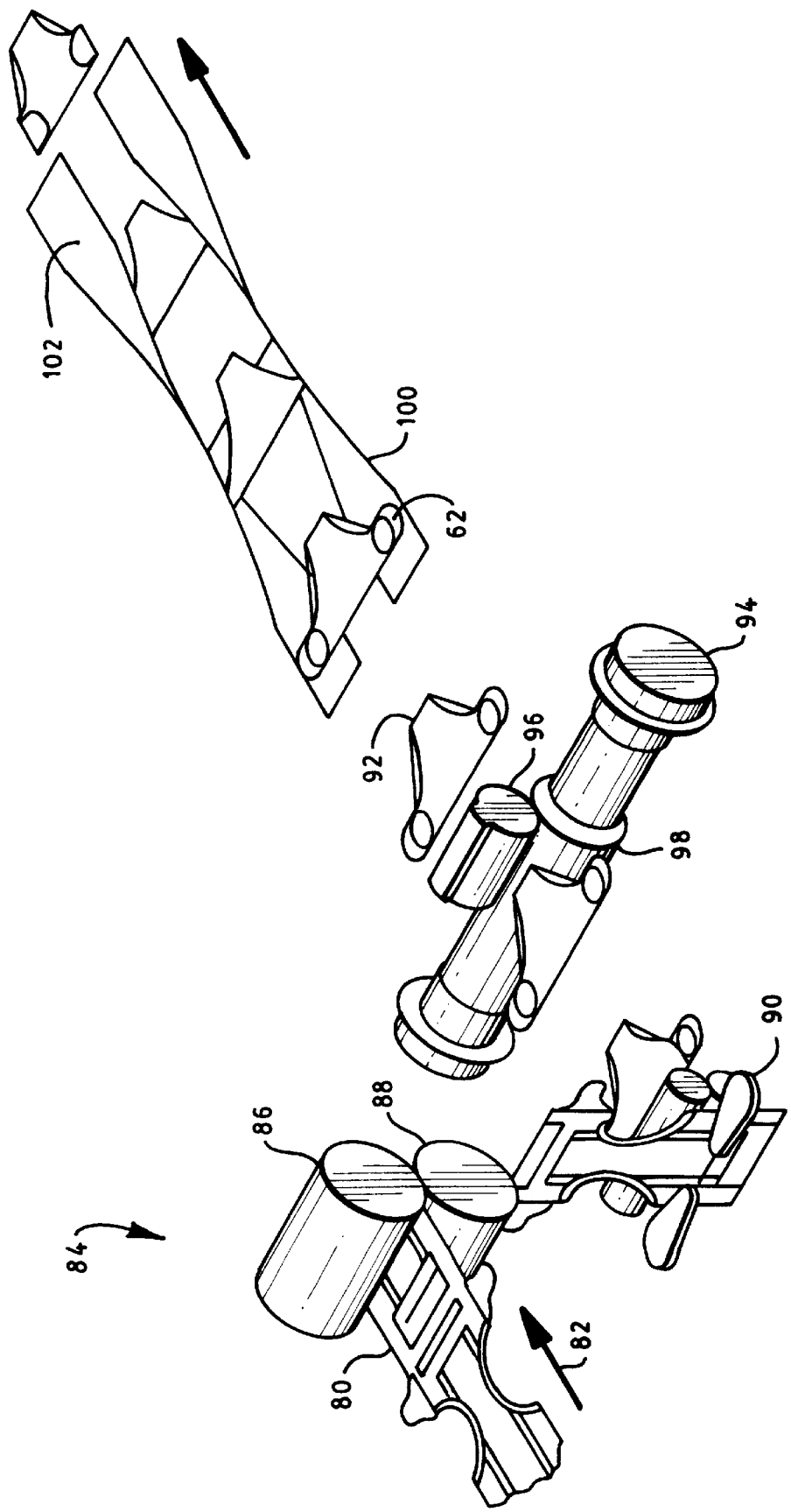
FIG. 1 representatively shows a schematic view of an example of a method of making a prefastened disposable absorbent article.
Figure 2:
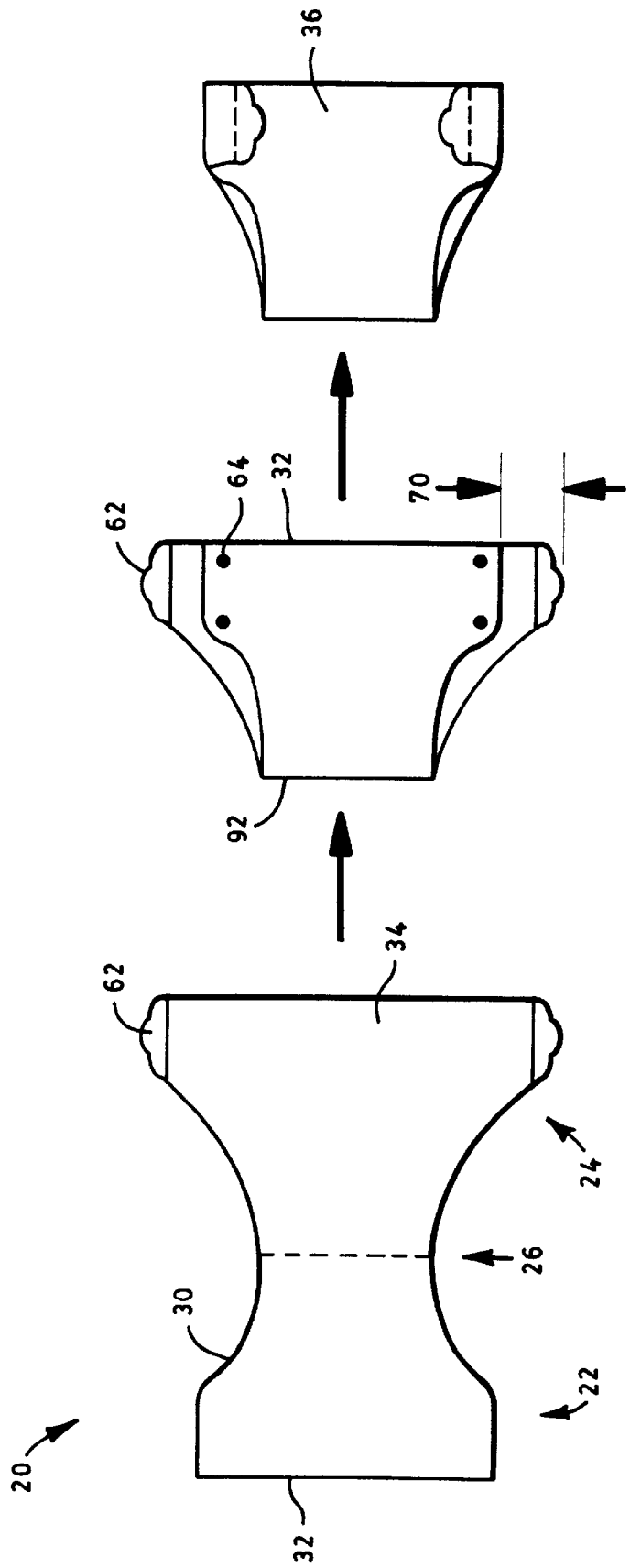
FIG. 2 representatively shows a plan view of the steps involved in the method of FIG. 1.
Figure 3:
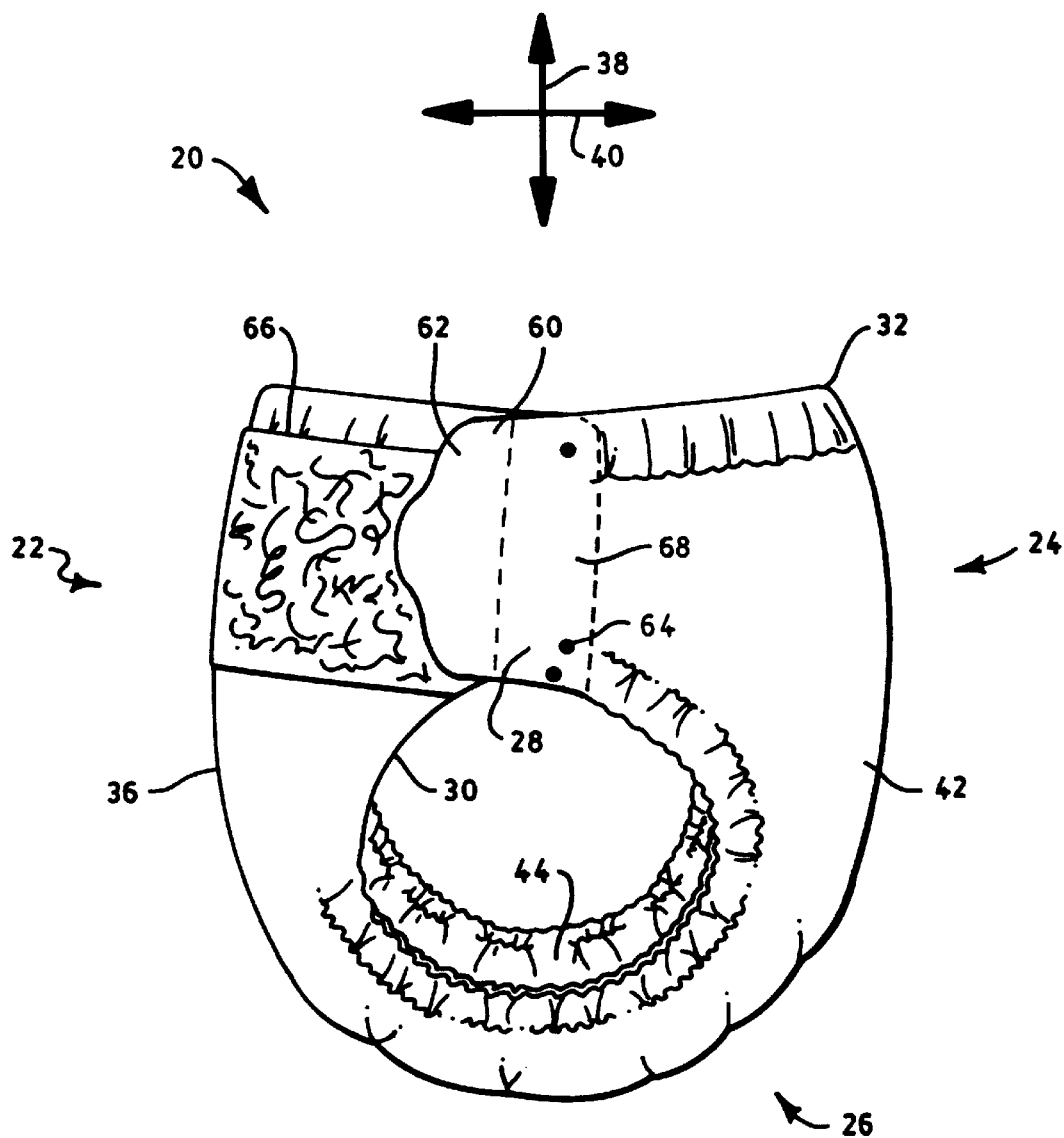
FIG. 3 representatively shows a side view of an example of a prefastened disposable absorbent article made according to the methods of the present invention.
Figure 4:
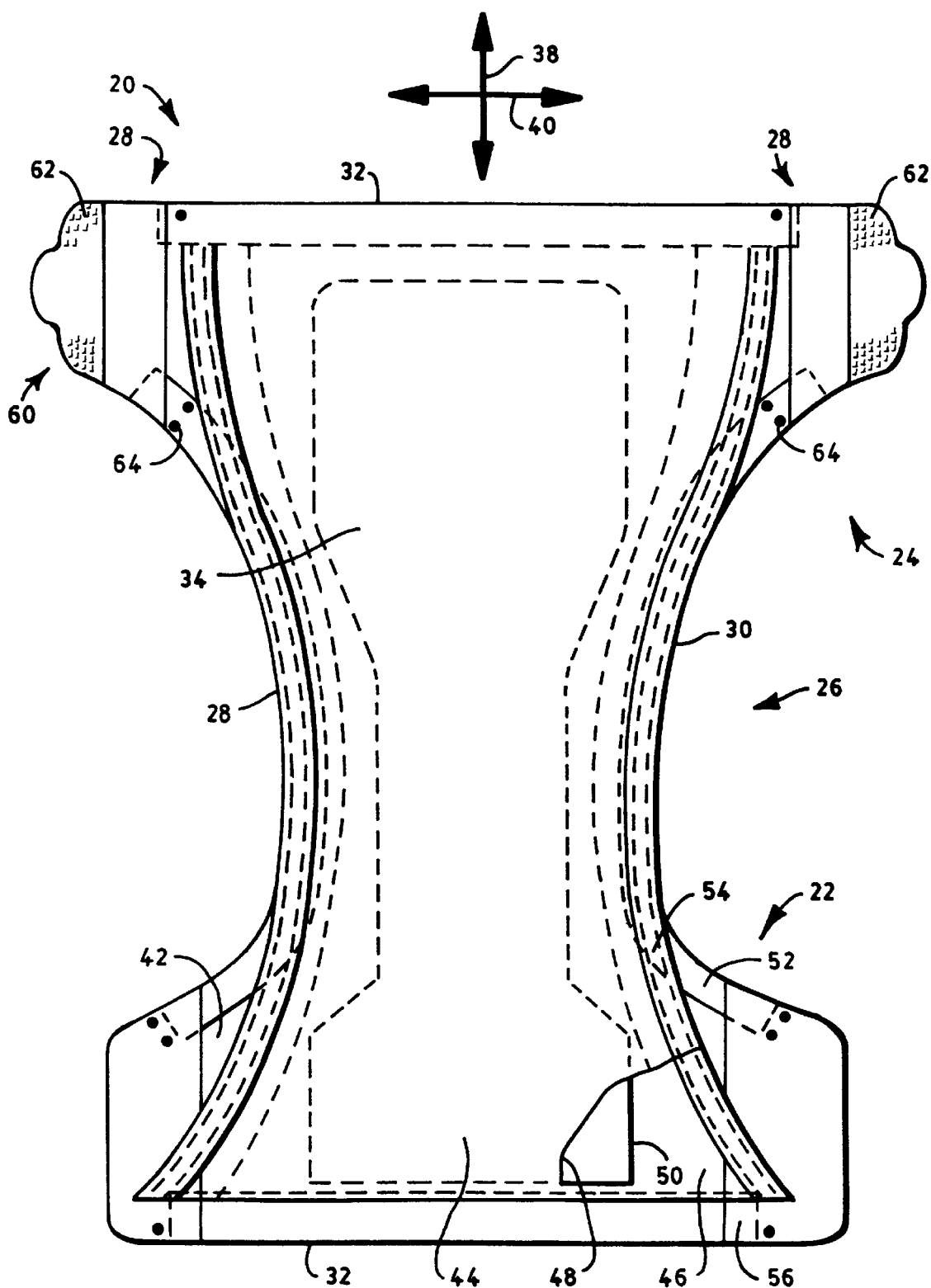
FIG. 4 representatively shows a plan view of the disposable absorbent article of FIG. 3 in an unfastened, stretched and laid flat condition with the surface of the article which contacts the wearer facing the viewer.
Figure 5:
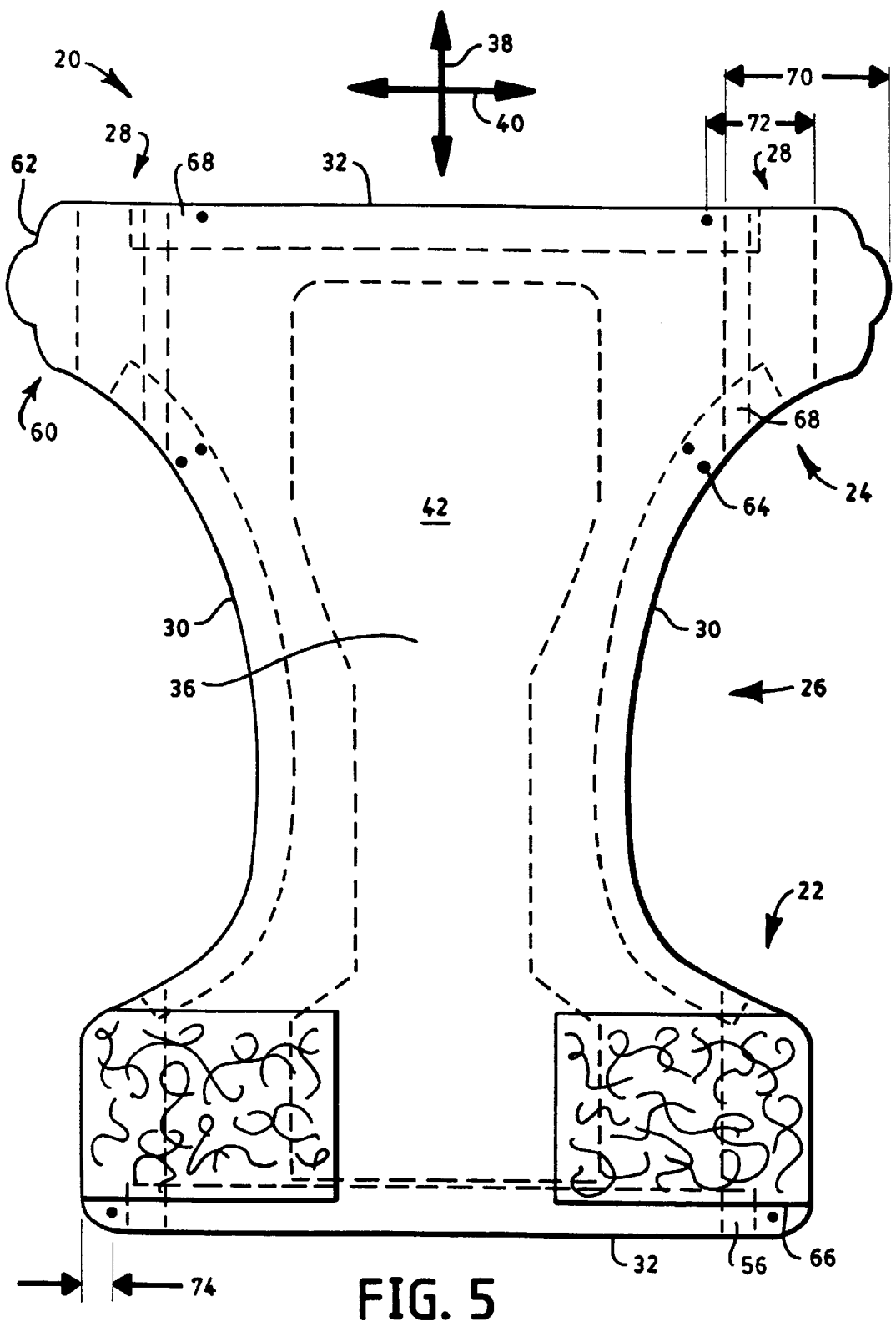
FIG. 5 representatively shows a plan view of the disposable absorbent article of FIG. 3 in an unfastened stretched and laid flat condition with the surface of the article which contacts the wearer's clothing facing the viewer.

FIGS. 1 and 2 representatively illustrate an example of a method of making a prefastened disposable absorbent article according to the present invention. FIG. 3 further representatively illustrates an example of a prefastened disposable diaper, as generally indicated at 20, made according to the methods of the present invention. FIGS. 4 and 5 representatively illustrate the diaper of FIG. 3 in an unfastened, laid flat condition. As illustrated in FIGS. 3–5, the diaper 20 defines a front waist region 22, a back waist region 24, a crotch region 26 which extends between and connects the front and back waist regions 22 and 24 and a pair of laterally opposed ear regions 28 integral with or connected to the back waist region 24. The diaper 20 further defines a pair of laterally opposed side edges 30, a pair of longitudinally opposed waist edges 32, an interior surface 34 which is configured to contact the wearer, an outer surface 36 opposite the interior surface 34, a longitudinal direction 38 and a lateral direction 40.

The front waist region 22 comprises the portion of the diaper 20 which, when worn, is positioned on the front of the wearer while the back waist region 24 comprises the portion of the diaper 20 which, when worn, is positioned on the back of the wearer. The crotch region 26 of the diaper 20 comprises the portion of the diaper 20 which, when worn, is positioned between the legs of the wearer and covers the lower torso of the wearer. The ear regions 28 comprise the portions of the diaper which, when worm, are positioned on the side hip regions of the wearer. The laterally opposed side edges 30 of the diaper 20 generally define leg openings which may be curvilinear. The waist edges 32 of the diaper 20 are configured to encircle the waist of the wearer when worn and provide a waist opening when fastened which defines a waist perimeter dimension.

The illustrated diaper 20 includes an outer cover 42, an absorbent chassis 44, a multi-functional fastening system 60 which includes a pair of primary fasteners 62 and a pair of laterally opposed releasable side bonds 64. The absorbent chassis 44 is configured to contain and/or absorb any body exudates discharged from the wearer. Whereas, the outer cover 42 and fastening system 60 are configured to maintain the diaper 20 about the waist of the wearer, conceal the absorbent chassis 44 from view, and provide a garment-like appearance. The diaper 20 may further include leg elastics 52, containment flaps 54 and waist elastics 56 as are known to those skilled in the art. It should be recognized that individual components of the diaper 20 may be optional depending upon the intended use of the diaper 20.

The methods of the different aspects of the present invention are directed at reliably and consistently providing prefastened disposable absorbent articles such as that representatively illustrated in FIG. 3. For example, as representatively illustrated in FIGS. 1 and 2, the methods can include providing a continuous web of interconnected diapers 80 moving in the direction indicated by arrow 82. In such a configuration, the front waist region 22 of the leading diaper 20 may be connected to the back waist region 24 of the trailing diaper 20 to form the continuous web of interconnected diapers 80. Alternatively, the back waist region 24 of the leading diaper may be connected to the front waist region 22 of the trailing diaper or the diapers may be arranged in a front-to-front/back-to-back relationship.

The continuous web of interconnected diapers 80 may be provided by means known to those skilled in the art. For example, a web of interconnected diapers 80, such as that illustrated in FIGS. 3–5, may be provided by first providing a continuously moving web of material for the outer cover 42. Individual absorbent chassis 44 for each diaper 20 may then be intermittently connected to the continuously moving web of outer cover material. The primary fasteners 62 are intermittently attached to the moving web of outer cover material. For example, the primary fasteners 62 may be attached to the laterally opposed side edges 30 of the diaper 20 in the back waist region 24 of the diaper 20. Additional components, such as the leg elastics 52, containment flaps 54 and waist elastics 56, may also be connected to the continuously moving web of outer cover material or the absorbent chassis 44 to provide the web of interconnected diapers 80.

The different components of the diaper 20 may be connected together by any means known to those skilled in the art such as, for example, adhesive, thermal or ultrasonic bonding. Desirably, most of the components are connected using ultrasonic bonding for improved manufacturing efficiency and reduced raw material cost.

The continuous web of interconnected diapers 80 is passed through cutter 84 which selectively cuts the web 80 into discrete, individual diapers 20. Such cutters are generally known to those skilled in the art and may include, for example, the combination of a cutting roll 86 and anvil roll 88 through which the web 80 travels. The anvil roll 88 may include a hardened steel rotating roll while the cutting roll 86 may include one or more flexible hardened steel blades clamped on to another rotating roll. The pinching force between the blade on the cutting roll and the anvil roll creates the cut. The cutting roll 86 may have one or more blades depending upon the desired distance between the cuts. The cutter 84 may further be configured to provide a spacing between the individual cut pieces after they are cut. Such a spacing can be provided by transferring the cut pieces away from the cutter at a higher speed than the speed at which the web is provided to the cutter.

The discrete diapers 20 are then folded in a conventional blade folder 90 about fold line 92 on the diaper 20. As such, the waist regions 22 and 24 of each diaper are positioned in a facing relationship with the primary fasteners 62 extending laterally outward beyond the side edges 30 of the diaper 20 as illustrated in FIGS. 1 and 2. The fold line 92 extends in a lateral direction through the crotch region 26 of the diaper 20. Desirably, each diaper 20 is consistently folded about fold line 92 such that the waist edges 32 of the diaper 20 in the front and back waist region 22 and 24 align with each other.

Suitable blade folders to provide the folding are well known to those skilled in the art. For example, as illustrated in FIG. 1, the blade folder 90 may include a pair of rotating folding blades which are configured to contact the diaper 20 along the fold line 92. In such a configuration, the rotation of the folding blades force the diaper into a nip between two rotating rolls causing the diaper 20 to fold about the fold line 92.

As illustrated in FIG. 1, the waist regions 22 and 24 are maintained in the facing relationship by passing the diaper 20 through bonder 94. Bonder 94 is configured to releasably bond the front and back waist region 22 and 24 at bond points 64 as representatively illustrated in FIG. 2. The term "releasably bond" as used herein refers to a bond which has a relatively low peak peel strength such that the bond can be broken by the caregiver if desired to assist in removing the diaper 20 from the wearer without tearing or severely damaging the other portions of the diaper 20. The bonds 64 may also be broken prior to applying the diaper to the wearer if it is desired to apply the diaper in a similar manner to conventional diapers instead of pulling it on over the legs and hips of the wearer. The specific values of the desired peel strength of the releasable bonds are set forth herein.

The releasable bonds 64 assist in maintaining the diaper 20 in the prefastened configuration while it is being pulled on or off over the hips of the wearer. The releasable bonds 64 further help stabilize and maintain the waist edges 32 of the diaper 20 in alignment after the diaper is folded. The releasable bonds 64 also provide improved hip coverage and prevent rollover or folding of the side edges 30 and waist edges 32 of the prefastened diaper 20 as it is pulled over the wearers hips. Such prevention of rollovers and foldovers can reduce the level of contact between the fasteners and the skin of the wearer which can desirably result in reduced skin irritation and redness.

Suitable bonding equipment which can be used to provide the releasable bonds 64 is well known to those skilled in the art. Desirably, the bonder 94 is an ultrasonic bonder for improved efficiency and cost effectiveness. For example, as illustrated in FIG. 1, the bonder 94 may include a rotary ultrasonic horn 96 and an anvil roll 98 between which the folded diapers 20 are passed to provide the releasable bonds 64. Suitable rotary ultrasonic horns are described in U.S. Pat. No. 5,110,403 to Ehlert, the disclosure of which is hereby incorporated by reference. Such rotary ultrasonic horns 96 generally have a diameter of from about 5 to about 20 centimeters and a width of from about 2 to about 15 centimeters. Alternatively, the ultrasonic horn 96 may be a stationary ultrasonic horn as are also known to those skilled in the art. Other suitable ultrasonic horns and ultrasonic bonders are commercially available from Branson Sonic Power Company, a business having offices in Danbury, Conn. The bonder 94 could otherwise be a thermal or adhesive bonder as are well known.

The bonder 94 may be configured to provide the releasable bonds 64 in a variety of patterns and shapes or sizes. For example, the releasable bonds 64 may be provided as a pattern of points, dots, circles, squares, triangles and the like which may be arranged in a linear or nonlinear configuration. In the illustrated embodiments, such patterns may be located on the bonding horn 96 or the anvil roll 98. Desirably, the pattern is located on the anvil roll 98 for improved manufacturing efficiency. The releasable bonds 64 may be ultrasonic, thermal, adhesive, cohesive, magnetic, mechanical and the like or combinations thereof.

As representatively illustrated in FIG. 1, the folded diaper 20 with the releasable bonds 64 is then passed into ear folder 100 to fold the primary fasteners 62 over into an engaging relationship with the opposite waist region of the diaper 20 to provide the prefastened diaper 20. To accomplish the folding, the ear folder 100 includes folding boards 102 which are configured to accept the primary fasteners 62 in a laid out flat condition and fold them inward and on to the outer surface 36 of the diaper 20 in the waist region opposite the waist region to which the fasteners are attached. As described below, the primary fasteners 62 may directly engage the outer cover 42 of the diaper 20 in the opposite waist region or, in the alternative, each diaper 20 may include an attachment panel 66 located on the opposite waist region to which the primary fasteners 62 can releasably engage. The diaper 20 may also be passed between a pair of rotating nip rolls (not shown) to assist in engaging the primary fasteners 62 to the opposite waist region.

The absorbent articles made by the methods of the present invention may be manufactured from a variety of materials. For example, as representatively illustrated in FIGS. 3–5, the outer cover 42 of the diaper 20 may suitably be composed of a material which is either liquid permeable or liquid impermeable. Since the absorbent chassis 44 of the different aspects of the present invention is designed to contain the body exudates discharged from the wearer, it is generally not necessary that the outer cover 42 be liquid impermeable. For example, the outer cover 42 may include various woven or nonwoven materials such as spunbond material, meltblown material, cotton material, rayon material or combinations thereof such as a spunbond-meltblown-spunbond (SMS) laminate material. The outer cover 42 may otherwise be at least partially liquid impermeable to further prevent any leakage of body exudates. For example, a typical outer cover 42 can be manufactured from a thin plastic film or other flexible liquid-impermeable material, woven or nonwoven fibrous layers, microporous "breathable" materials, elastic materials and combinations thereof.

The absorbent chassis 44 of the diaper 20 is suitably connected to the outer cover 42 to provide the disposable diaper 20. The absorbent chassis 44 may be connected to the outer cover 42 in manners well known to those skilled in the art. For example, the absorbent chassis 44 may be bonded to the outer cover 42 using adhesive, thermal or ultrasonic bonding techniques known to those skilled in the art. Alternatively, the absorbent chassis 44 may be connected to the outer cover 42 using conventional fasteners such as buttons, hook and loop type fasteners, adhesive tape fasteners, and the like. The other components of the diaper 20 may be suitably connected together using similar means.

Desirably, the absorbent chassis 44 is connected to the outer cover 42 only at or adjacent the waist edges 32 of the outer cover 42 thereby creating a front attached portion, a back attached portion and an unattached portion which extends between and connects the attached portions. The unattached portion of the absorbent chassis 44 remains substantially unattached to the outer cover 42 and is generally configured to fit between the legs of the wearer and at least partially cover the lower torso of the wearer. Thus, the unattached portion is generally the portion of the absorbent chassis 44 which is configured to initially receive the body exudates from the wearer when in use. In this manner, the absorbent chassis 44 is connected to the outer cover 42 to secure the chassis 44 in place while not adversely restricting the movement of the outer cover 42 in use. Alternatively, the absorbent chassis 44 may be attached to the outer cover 42 along the entire longitudinal length of the absorbent chassis 44 or any portion thereof or along only the outer periphery of the absorbent chassis 44.

As representatively illustrated in FIG. 4, the absorbent chassis 44 according to the present invention may include a backsheet 46, a bodyside liner 48 which is connected to the backsheet 46 in a superposed relation, and an absorbent core 50 which is located between the bodyside liner 48 and the backsheet 46. In alternative configurations wherein the outer cover 42 is at least partially resistant to the flow of liquids therethrough, the backsheet 46 may optionally be omitted from the absorbent chassis 44.

The absorbent chassis 44 is generally conformable and capable of absorbing and retaining body exudates. The absorbent chassis 44 may have any of a number of shapes and sizes. For example, as representatively illustrated in FIG. 4, the absorbent chassis 44 may be rectangular, I-shaped or T-shaped. The size and absorbent capacity of the absorbent chassis 44 should be compatible with the size of the intended wearer and the fluid loading imparted by the intended use of the diaper 20. Typically, it is desirable that the absorbent chassis 44 have an absorbent capacity of at least about 300 grams of urine. It is generally preferred that the absorbent chassis 44 be narrower in the crotch region 26 than in the waist regions 22 and 24. It has been found that the absorbent chassis 44 of the present invention is particularly useful when the width dimension in the crotch region 26 is from about 2.5 to about 10.2 centimeters (1.0 to about 4.0 inches), desirably no more than about 7.6 centimeters (3.0 inches) and more desirably no more than about 5.1 centimeters (2.0 inches). The narrow crotch width dimension of the absorbent chassis 44 allows the absorbent chassis 44 to better fit between the legs of the wearer.

The bodyside liner 48 of the absorbent chassis 44, as representatively illustrated in FIG. 4, suitably presents a bodyfacing surface which is intended to be worn adjacent the body of the wearer and is compliant, soft feeling and nonirritating to the wearers skin. Further, the bodyside liner 48 may be less hydrophilic than the absorbent core 50, to present a relatively dry surface to the wearer, and may be sufficiently porous to be liquid permeable, permitting liquid to readily penetrate through its thickness. A suitable bodyside liner 48 may be manufactured from a wide selection of web materials, such as woven and nonwoven fabrics, porous foams, reticulated foams, apertured plastic films, natural fibers (for example, wood or cotton fibers), synthetic fibers (for example, polyester or polypropylene fibers), or a combination of natural and synthetic fibers. The bodyside liner 48 is suitably employed to help isolate the wearer's skin from fluids held in the absorbent core 50 of the absorbent chassis 44.

The backsheet 46 of the absorbent chassis 44, as representatively illustrated in FIG. 4, may suitably be composed of a material which is either liquid permeable or liquid impermeable. It is generally preferred that the backsheet 46 be formed from a material which is substantially impermeable to fluids. A typical backsheet can be manufactured from a thin plastic film or other flexible liquid-impermeable material. The backsheet 46 may also be constructed of a material which is similar to the material described as being suitable for the outer cover 42.

The bodyside liner 48 and backsheet 46 are generally adhered to one another so as to form a pocket in which the absorbent core 50 is located to provide the absorbent chassis 44. The bodyside liner 48 and backsheet 46 may be adhered directly to each other around the outer periphery of the absorbent chassis 44 by any means known to those skilled in the art such as adhesive bonds, sonic bonds or thermal bonds. For example, a uniform continuous layer of adhesive, a patterned layer of adhesive, a sprayed or meltblown pattern of adhesive or an array of lines, swirls or spots of adhesive may be used to affix the bodyside liner 48 to the backsheet 46. It should be noted that both the bodyside liner 48 and the backsheet 46 need not extend completely to the outer periphery of the absorbent chassis 44. For example, the backsheet 46 may extend to the outer periphery of the absorbent chassis 44 while the bodyside liner 48 may be attached to the backsheet 46 inboard of the outer periphery of the absorbent chassis 44, or more towards the longitudinal centerline of the diaper 20. In alternative configurations, especially wherein the backsheet 46 is omitted, the bodyside liner 48 may be suitably adhered directly to the absorbent core 50 or to the outer cover 42.

The absorbent core 50, as representatively illustrated in FIG. 4, is positioned between the bodyside liner 48 and the backsheet 46 to form the absorbent chassis 44. The absorbent core 50 is desirably conformable and capable of absorbing and retaining body exudates. The absorbent core 50 may have any of a number of shapes and sizes. For example, the absorbent core may be rectangular, I-shaped or T-shaped. It is generally preferred that the absorbent core 50 be narrower in the crotch region 26. The size of the absorbent core 50 should be compatible with the size of the intended wearer and the desired absorbent capacity of the absorbent chassis 44.

The absorbent core 50 of the absorbent chassis 44 may suitably comprise various types of wettable, hydrophilic fibrous materials. Examples of suitable materials include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester and polyamide fibers; and synthetic fibers composed of a nonwettable thermoplastic polymer, such as polypropylene fibers, which have been hydrophilized by appropriate means known to those skilled in the art. The absorbent core 50 may also comprise selected blends of the various types of fibers mentioned above.

In a particular aspect of the invention, the absorbent core 50 may include a matrix of hydrophilic fibers, such as a web of cellulosic fibers, mixed with particles of a high-absorbency material such as that commonly known as superabsorbent material. As used herein, the term "high-absorbency material" refers to materials that are capable of absorbing at least 10 times their own weight in liquid. In a particular embodiment, the absorbent core 50 comprises a mixture of superabsorbent hydrogel-forming particles and wood pulp fluff. The wood pulp fluff may be exchanged with synthetic, polymeric, meltblown fibers or with a combination of meltblown fibers and natural fibers. The high-absorbency material may be substantially homogeneously mixed with the hydrophilic fibers or may be nonuniformly mixed. The high-absorbency material may also be arranged in a generally discrete layer within the matrix of hydrophilic fibers. Alternatively, the absorbent core 50 may comprise a laminate of fibrous webs and high-absorbency material or other suitable means of maintaining a high-absorbency material in a localized area.

As representatively illustrated in FIG. 4, the absorbent chassis 44 of the disposable diaper 20 may include a pair of containment flaps 54 which are configured to provide a barrier to the lateral flow of body exudates. The containment flaps 54 may be located along the laterally opposed side edges of the absorbent chassis 44. Each containment flap 54 typically defines an unattached edge which is configured to maintain an upright, perpendicular configuration in at least the crotch region 26 of the diaper 20 to form a seal against the wearer's body. The containment flaps 54 may extend longitudinally along the entire length of the absorbent chassis 44 or may only extend partially along the length of the absorbent chassis 44. When the containment flaps 54 are shorter in length than the absorbent chassis 44, the containment flaps 54 can be selectively positioned anywhere along the side edges of the absorbent chassis 44. In a particular aspect of the invention, the containment flaps 54 extend along the entire length of the absorbent chassis 44 to better contain the body exudates.

Such containment flaps 54 are generally well known to those skilled in the art. For example, suitable constructions and arrangements for containment flaps 54 are described in U.S. Pat. No. 4,704,116 issued Nov. 3, 1987, to K. Enloe the disclosure of which is hereby incorporated by reference.

The disposable diaper 20 of the different aspects of the present invention may further include elastics at the waist edges 32 and side edges 30 of the diaper 20 to further prevent the leakage of body exudates and support the absorbent chassis 44. For example, as representatively illustrated in FIG. 4, the diaper 20 of the present invention may include a pair of leg elastic members 52 which are connected to the laterally opposed side edges 30 in the crotch region 26 of the diaper 20 and a pair of waist elastic members 56 which are connected to the longitudinally opposed waist edges 32 of the diaper 20. The leg elastics 52 and waist elastics 56 are generally adapted to fit about the legs and waist of a wearer in use to maintain a positive, contacting relationship with the wearer to effectively reduce or eliminate the leakage of body exudates from the diaper 20.

Materials suitable for use as the leg elastics 52 and waist elastics 56 are well known to those skilled in the art. Exemplary of such materials are sheets or strands or ribbons of a polymeric, elastomeric material which are adhered to the outer cover 42 in a stretched position, or which are attached to the outer cover 42 while the outer cover is pleated, such that elastic constrictive forces are imparted to the outer cover 42. The leg elastics may also include such materials as polyurethane, synthetic and natural rubber.

The absorbent article of the different aspects of the present invention further includes a multi-functional fastening system 60 for securing the absorbent article about the waist of the wearer. The multi-functional fastening system 60 includes fasteners located on one of the waist regions 22 and 24 of the diaper 20 which are configured to releasably engage the opposite waist region of the diaper 20 to maintain the diaper about the waist of the wearer. The use of fasteners which are refastenable or releasably engageable allows for ease of securing and removing the diaper 20 from the waist of the wearer without undesirably soiling the wearer.

As representatively illustrated in FIGS. 3–5, the multi-functional fastening system 60 of the present invention may include a pair of primary fasteners 62 which are located on the side edges 30 of the diaper 20 in the back waist region 24 of the diaper 20. In such a configuration, the primary fasteners 62 are configured to encircle the hips of the wearer and engage the outer surface 36 of the front waist region 22 of the diaper 20 to maintain the diaper 20 on the wearer. Alternatively, the primary fasteners 62 may be located on the front waist region 22 and may be configured to releasably engage the outer surface 36 of the back waist region 24 of the diaper 20. The primary fasteners 62 may be adhered to the side edges 30 by any means known to those skilled in the art such as adhesive bonds, sonic bonds or thermal bonds.

Desirably, the primary fasteners 62 are releasably engageable directly with the outer surface of the outer cover 42 of the diaper 20 to provide improved ease of fastening. In such an arrangement, the primary fasteners 62 can be secured anywhere on the outer cover 42 and the diaper 20 may be able to fit a wider variety of sizes and shapes. Alternatively, as representatively illustrated in FIG. 3, the disposable diaper 20 of the present invention may further include an attachment panel 66 located on the outer cover 42 in one of the waist regions 22 and 24 of the diaper 20. In such a configuration, the primary fasteners 62 are releasably engageable with the attachment panel 66 to maintain the diaper 20 about the waist of the wearer. When the primary fasteners 62 are releasably engaged, the side edges 30 of the diaper 20 define leg openings which are configured to encircle the legs of the wearer and the waist edges 32 define a waist opening which is configured to encircle the waist of the wearer. As illustrated in FIG. 3, the attachment panel 66 may include two separate panels located along the opposite side edges in one of the waist regions 22 and 24 of the diaper 20. Alternatively, the attachment panel 66 may include a single piece of material which extends substantially across the respective waist region of the diaper 20.

In the different aspects of the present invention, the primary fasteners 62 are releasably engaged with the outer surface of the opposite waist region 22 and 24 of the diaper 20 before the diaper 20 is placed on the wearer to provide a prefastened diaper. In such a configuration, the prefastened diaper 20 can be pulled on or off over the legs and hips of the wearer. If the diaper 20 becomes soiled during use, the primary fasteners 62 can be disengaged to easily remove the diaper 20 from the waist of the wearer with reduced risk of undesirably soiling the clothes or legs of the wearer. Thus, in such a configuration, the diaper 20 of the different aspects of the present invention can be pulled on or off over the hips of the wearer such as conventional training pants and can be readily removed by disengaging the fasteners similar to conventional diaper articles. Alternatively, the care giver may disengage the prefastened primary fasteners 62 prior to applying the diaper 20 to the wearer if it is desired to apply the diaper 20 of the invention similar to the manner in which conventional diapers are applied to the wearer.

Suitable fasteners are well known to those skilled in the art and can include adhesive tape tab fasteners, hook and loop fasteners, mushroom fasteners, snaps, pins, belts and the like, and combinations thereof. For example, as representatively illustrated in FIG. 4, the primary fasteners 62 may be hook type fasteners and the outer cover 42 or attachment panel 66 may be configured to function as a complimentary loop type fastener. Desirably, the fasteners 62 are hook type fasteners which are releasably engageable directly with the outer cover 42. Such an arrangement provides the ability to vary the size of the waist opening in very small increments over a wide range to fit the waist of the wearer.

The multi-functional fastening system 60 on the disposable diaper 20 of the present invention may further include at least one secondary fastener (not shown) to provide improved securement of the diaper 20 about the waist of the wearer when the primary fasteners 62 are releasably engaged. Such a secondary fastener can be configured to further conform the waist regions 22 and 24 of the diaper 20 to the waist of the wearer. A suitable arrangement for such secondary fasteners is described in U.S. patent application Ser. No. 08/907,585 entitled "A MULTI-FUNCTIONAL FASTENER FOR DISPOSABLE ABSORBENT ARTICLES" and filed Aug. 8, 1997 in the name of J. Suprise set forth above. Alternatively, in embodiments wherein the secondary fasteners are omitted, the primary fasteners 62 are capable of being reengaged after the diaper is pulled on to further conform the waist regions of the diaper to the waist of the wearer.

The use of such secondary fasteners has been found to be particularly desirable since the primary fasteners 62 are releasably engaged with the respective waist region of the diaper 20 prior to use. In such a configuration, the waist opening of the diaper 20 when the primary fasteners 62 are engaged must be sufficient to allow the prefastened diaper 20 to be pulled over the hips of the wearer. However, the circumference of the waist of the wearer is typically less than the circumference around the hips of the wearer. Thus, the waist opening of the prefastened diaper 20 may not conform to the waist of the wearer which may undesirably result in leaks. In such a configuration, the secondary fastener of the diaper 20 is configured to conform the waist regions of the diaper 20 to the wearer by reducing the waist perimeter dimension of the diaper 20 after the prefastened diaper is pulled on the wearer. Thus, the care giver is not required to reposition the primary fasteners 62 to conform the waist regions 22 and 24 to the waist of the wearer. As a result, when the diaper 20 is to be removed from the wearer, the care giver may simply disengage the secondary fastener if necessary and pull the prefastened diaper down over the hips and legs of the wearer without having to reposition the primary fasteners 62. Alternatively, the care giver may disengage both the secondary and the primary fasteners to remove the diaper 20 in a manner which is similar to removing conventional diapers.

As described above in connection with the description of the method aspects of the invention, the prefastened absorbent article of the different aspects of the present invention further includes a pair of releasable side bonds for improved reliability of maintaining the article in the prefastened condition particularly when it is being pulled on or off over the hips of the wearer. Absorbent articles including such releasable side bonds are further described in U.S. patent application Ser. No. 08/100,574 entitled "DISPOSABLE ABSORBENT ARTICLES HAVING PASSIVE SIDE BONDS AND ADJUSTABLE FASTENING SYSTEMS" filed in the name of Elsberg on the same date as the instant application and having Attorney Docket No.13,611, the disclosure of which is hereby incorporated by reference. For example, as representatively illustrated in FIG. 3, the diaper 20 may include a pair of releasable side bonds 64 which releasably connect an overlapped portion 68 of the back waist region 24 or opposed ear regions 28 to the front waist region 22 of the diaper 20. In such a configuration, the releasable side bonds 64 assist the fastening system 60 in maintaining the diaper 20 in a prefastened condition as the diaper 20 is pulled up or down over the hips of the wearer. Moreover, the releasable side bonds 64 prevent movement and shifting of the waist regions 22 and 24 and ear regions 28 relative to each other for improved fit and performance. The releasable side bonds 64 also prevent rollover or folding of the side edges 30 and waist edges 32 of the prefastened diaper 20 as it is pulled over the wearers hips.

As shown in the illustrated embodiments, the releasable side bonds 64 are located inward of the primary fasteners 62 on the back waist region 24 of the diaper 20. As used herein, the term "inward" refers to a distance in the lateral direction 40 towards a longitudinal centerline of the diaper 20. In such a configuration, the releasable side bonds 64 connect the overlapped portion 68 of the back waist region 24 inward of the primary fasteners 62 to the front waist region 22. Desirably, the releasable side bonds 64 connect the overlapped portion 68 of the back waist region 24 to the side edge 30 of the front waist region 22. For example, the releasable side bonds 64 may bond a waist edge 32 and side edge 30 of the back waist region to the side edge 30 of the front waist region 22. In such a configuration, the releasable bonds 64 also assist in preventing the side and waist edges 30 and 32 of the diaper 20 from rolling over as the diaper 20 is pulled on or taken off.

As illustrated in FIGS. 2 and 5, the overlapped portion 68 of the back waist region 24 defines an overlap distance 70 which is the distance between the respective side edges 30 of the front and back waist regions 22 and 24 when the diaper is prefastened. The overlap distance 70 is important to ensure that a good seal is provided around the legs and waist of the wearer. Moreover, the greater the overlap distance 70, the further inward the releasable bonds 64 can be located which can provide improved reduction in the relative movement between the front and back waist regions 22 and 24 during use. To provide such improved fit and performance, it is desirable that the overlap distance 70 be at least about 0.5 centimeters and more desirably at least about 1.0 centimeters. As illustrated in FIG. 4, the passive bonds 64 may also be located on the opposite waist region a distance inward form the side edge 30 of about 0.5 to about 4.0 centimeters for improved attachment and performance.

As illustrated in FIG. 5, the releasable side bonds 64 are located on the back waist region 24 inward from the primary fastener 62 a distance 72 to prevent the relative movement or shifting between the front and back waist regions 22 and 24 with respect to each other. In a particular embodiment, at least a portion of the releasable side bonds 64 is located laterally inward from the primary fastener 62 a distance 72 of at least about 1.0 centimeters and desirably at least about 2.0 centimeters. When the distance 72 is less than the values set forth above, the front and back waist regions 22 and 24 may undesirably shift with respect to each other during the application or use of the diaper 20. Such shifting of the respective waist regions 22 and 24 of the diaper 20 can adversely affect the fit of the diaper 20 on the wearer which can undesirably lead to increased leakage. As illustrated in FIG. 5, the passive bonds 64 may also be located on the opposite waist region a distance 74 inward form the side edge 30 of about 0.2 to about 2.5 centimeters for improved attachment and performance.

In certain aspects of the invention, the location of the side bonds 64 and the respective distance 72 and overlap distance 70 can be selectively varied to tailor the fit of the diaper 20 for different sized wearers. For example, the location of the bonds 64 may be varied during the manufacturing process such that the same process can produce prefastened diapers for use in conventional Step 3 or Step 4 sizes.

The releasable side bonds 64 connect the respective front and back waist regions 22 and 24 in a facing relationship. For example, in the illustrated embodiments, the releasable side bonds 64 connect the interior surface 34 of the diaper 20 in the rear waist region 24 to the interior surface 34 of the diaper 20 in the front waist region 22. Such a configuration can lead to improved manufacturability. In such a configuration, the overlapped portions 68 of the rear waist region 24 may be folded over to engage the primary fasteners 62 about a line which is adjacent to, inward from or outward from the side edges 30 of the diaper 20 in the front waist region 22. For example, the overlapped portions 68 of the rear waist region 24 may be folded over about a line which is inward from the side edges 30 of the diaper 20 in the front waist region such that the side edges 30 of the front waist region 22 are folded over on themselves when the primary fasteners 62 are engaged. In the illustrated embodiments, the overlapped portions 68 of the rear waist region 24 are folded over a line which is adjacent to the side edges 30 of the diaper 20 in the front waist region 22.

The releasable side bonds 64 are configured to assist the primary fasteners 62 in maintaining the diaper 20 in a prefastened configuration as the diaper 20 is pulled on and off over the hips of the wearer and during use. Thus, it is desirable that the releasable side bonds 64 provide adequate shear strength for assisting the primary fasteners 62. For example, in a particular embodiment, the releasable side bonds 64 define a shear strength of at least about 50 grams and desirably at least about 100 grams. For example, the side bonds 64 may define a shear strength of from about 100 to about 4000 grams and desirably from about 500 to about 2000 grams. As used herein, the term "shear strength" refers to the value obtained when subjecting the side bonds to the Shear Strength Test described herein. Shear strength values less than those described above may not prevent the separation of the front and rear waist regions 22 and 24 from each other during the application and use of the diaper 20.

The releasable side bonds 64 are also configured to be readily tearable such that the caregiver can easily pealingly remove the diaper 20 from the wearer after it has been soiled. Thus, it is desirable that the releasable side bonds 64 define a relatively low peak peel strength such that the caregiver can readily disengage the fasteners 62, break the releasable side bonds 64 and separate the front and back waist regions 22 and 24 to remove the diaper 20 from the waist of the wearer similar to conventional diapers which are not prefastened. For example, in a particular embodiment, the releasable side bonds 64 define a peel strength of no more than about 1500 grams, desirably no more than about 1000 grams, and more desirably no more than about 800 grams. As used herein, the term "peel strength" refers to the value obtained when subjecting the side bonds to the Peel Strength Test described herein. Peel strength values greater than those described above may not be readily tearable and may undesirably result in tearing of other portions of the diaper 20. Desirably, the releasable bonds 64 define a peel strength of no more than about 50 percent and more desirably no more than about 20 percent of the peel strength of the primary fasteners 62.

The different aspects of the present invention advantageously provide methods of maling a prefastened disposable absorbent article which includes the combination of releasable side bonds and an adjustable fastening system. The fastening system is prefastened to releasably engage the front and back waist portions to allow the absorbent article to be pulled up or down over the hips of the wearer such as conventional training pants. Moreover, the fastening system can be used to releasably engage and adjust the front and back waist portions of the absorbent article to maintain the absorbent article about the waist of the wearer after the article has been pulled on in a similar manner to conventional diapers. The releasable side bonds assist the fastening system in maintaining the article in a prefastened condition as the article is pulled up or down over the hips of the wearer. Moreover, the releasable side bonds prevent movement and shifting of the waist portions relative to each other for improved fit and performance. The releasable side bonds also prevent the rollover or folding on the side and waist edges of the prefastened absorbent article as it is pulled over the wearers hips.

As a result, the absorbent article of the present invention is designed to conform to the body of the wearer to effectively contain bodily exudates while still being capable of being reliably pulled up or down over the hips of the wearer to assist in the toilet training of the wearer. Moreover, similar to conventional diapers, the absorbent article of the present invention can advantageously be applied to and removed from the wearer with relative ease and cleanliness.

Peel Strength Test

This test method is designed to quantify, in grams, the peak strength of the ultrasonic point bonds holding the front waist region of the absorbent article to the rear waist region. The direction of removal (peel), in this application, is that direction in which the fastener material would generally be removed from a substrate when the product is in use. This direction is generally perpendicular to a longitudinal centerline of the product.

Equipment
1. Tensile tester capable of obtaining a peak load and equipped with an appropriate load cell. A suitable tensile testing system is a Sintech Tensile Tester, commercially available from MTS Sintech, Research Triangle Park, N.C., under the trade designation Instron Model 4201 Tensile Tester with Sintech QAD (Quality Assurance Department) Software.
2. Software commercially obtained from MTS Sintech under the trade designation Sintech Testworks™.
3. Pnuematic-action grips commercially available from Instron Corporation, Canton, Mass., under the trade designation "Instron Model 2712-004."
4. 1 by 4 inch grip faces, serrated, commercially available from Instron Corporation, Canton, Mass.
5. Test facility having a temperature of 23±1° C., and a relative humidity of 50±2 percent.

Test Procedure
1. A sample to be tested is conditioned in the test facility for at least 4 hours prior to testing.
2. The load cell is calibrated and the software loaded.
3. The grips are installed on the tensile tester with the jaws closed.
4. The test condition for the tensile tester are set as follow:

| | |
|---|---|
| Crosshead speed: | 500 millimeters/minute |
| Full-scale load: | 5 kilograms |
| Threshold: | 5 percent |
| Fail criterion: | 95 percent |
| Gage length: | 50 millimeters |

5. The weight of the clamp is tared out.

6. The primary fastener tab of the fastening element on the back waist region of the article is inserted into the upper jaw such that the edge of the grip face is flush with the inner edge of the hook material.
7. The front waist region of the article is inserted into the lower jaw such that the inner surface of the back waist region and the outer surface of the front waist region form a 180° angle. The lower jaw is closed.
8. The crosshead is started in motion.
9. The peak load of failure is recorded. It is intended that the mode of failure is that the back waist region of the diaper separates from the front waist region of the diaper. Results are rejected if the place of failure is any location other than the ultrasonic point bonds.

Shear Strength Test

This test method is designed to quantify, in grams, the peak dynamic shear strength of the ultrasonic point bonds holding the front waist region of the absorbent article to the rear waist region. The direction of force in this application is generally perpendicular to the longitudinal centerline of the product.

Equipment
1. Tensile tester capable of obtaining a peak load and equipped with an appropriate load cell. A suitable tensile testing system is a Sintech Tensile Tester, commercially available from MTS Sintech, Research Triangle Park, N.C., under the trade designation Instron Model 4201 Tensile Tester with Sintech QAD (Quality Assurance Department) Software.
2. Software commercially obtained from MTS Sintech under the trade designation Sintech Testworks™.
3. Pnuematic-action grips commercially available from Instron Corporation, Canton, Mass., under the trade designation "Instron Model 2712-004."
4. 1 by 4 inch grip faces, serrated, commercially available from Instron Corporation, Canton, Mass.
5. Test facility having a temperature of 23±1° C., and a relative humidity of 50±2 percent.

Test Procedure
1. A sample to be tested is conditioned in the test facility for at least 4 hours prior to testing.
2. The load cell is calibrated and the software loaded.
3. The grips are installed on the tensile tester with the jaws closed.
4. The test condition for the tensile tester are set as follows:

| | |
|---|---|
| Crosshead speed: | 500 millimeters/minute |
| Full-scale load: | 5 kilograms |
| Threshold: | 5 percent |
| Fail criterion: | 95 percent |
| Gage length: | 50 millimeters |

5. The weight of the clamp is tared out.
6. The primary fastener tab of the fastening element on the back waist region of the article is inserted into the upper jaw such that the edge of the grip face is flush with the inner edge of the hook material.
7. The front waist region of the article is inserted into the lower jaw such that the inner surface of the back waist region and the inner surface of the front waist region are facing the same direction and are parallel to one another. The lower jaw is closed.

8. The crosshead is started in motion.

9. The peak load of failure is recorded. It is intended that the mode of failure is that the back waist region of the article separates from the front waist region of the article. Results are rejected if the place of failure is any location other than the ultrasonic point bonds.

While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

We claim:

1. A method of making a prefastened disposable absorbent article which defines an absorbent, a front waist region, a back waist region, a crotch region which extends between and connects said waist regions, a pair of opposed side edges and a pair of opposed waist edges; said method comprising:
   a) forming a continuous web of interconnected absorbent articles each of which includes a pair of primary fasteners which are located on said side edges of said article in one waist region of said article;
   b) selectively cutting said continuous web into discrete absorbent articles;
   c) folding each of said discrete absorbent articles about a fold line extending in a lateral direction through said crotch region of said article thereby positioning said waist regions in a facing relationship;
   d) releasably bonding said one waist region to an opposite waist region; and
   e) folding said primary fasteners over and onto said opposite waist region to releasably engage said opposite waist region to provide said prefastened absorbent article.

2. The method of claim 1 wherein said primary fasteners are hook type fasteners.

3. The method of claim 1 wherein said primary fasteners are located on said opposed side edges in said back waist region of said absorbent article and are folded over to releasably engage said front waist region to provide said prefastened absorbent article.

4. The method of claim 1 wherein said waist regions are releasably bonded together using at least two releasable point bonds.

5. The method of claim 4 wherein said releasable point bonds bond said waist edge and said side edge of said one waist region to said side edges of said opposite waist region.

6. The method of claim 1 wherein said side edges of said opposite waist region are releasably bonded to said one waist region at a location inward of said primary fasteners.

7. The method of claim 6 wherein said side edges of said opposite waist region are releasably bonded to said one waist region at a location on said opposite waist region inward from said side edges a distance of from about 0.2 to about 2.5 centimeters.

8. The method of claim 1 wherein said waist regions are releasably bonded together using ultrasonic bonding.

9. The method of claim 1 wherein said waist regions are releasably bonded to define a peel strength of no more than about 1500 grams.

10. The method of claim 1 wherein an interior surface of said absorbent article in said one waist region is releasably bonded to an interior surface of said absorbent article in said opposite waist region.

11. A method of making a prefastened disposable absorbent article which defines a front waist region, a back waist region, a crotch region which extends between and connects said waist regions, a pair of opposed side edges and a pair of opposed waist edges, said method comprising the steps of:
   a) providing a continuously moving web of outer cover material;
   b) intermittently connecting an absorbent chassis to said outer cover to provide a continuously moving web of interconnected absorbent articles each of which includes one of said absorbent chassis;
   c) intermittently attaching a pair of primary fasteners to said opposed side edges of said back waist region of each of said interconnected absorbent articles;
   d) selectively cutting said continuous web of interconnected absorbent articles into discrete absorbent articles;
   e) folding each of said discrete absorbent articles about a fold line extending in a lateral direction through said crotch region of said absorbent article thereby positioning said waist regions of said absorbent article in a facing relationship with said primary fasteners extending laterally outward beyond said side edges;
   f) releasably bonding said front waist region to said back waist region; and
   g) folding said primary fasteners over and onto said front waist region to releasably engage said front waist region to provide said prefastened absorbent article.

12. The method of claim 11 wherein said primary fasteners are hook type fasteners.

13. The method of claim 11 wherein said step of folding said absorbent article about said fold line comprises folding said absorbent article to position said waist edges of said waist regions in alignment with each other.

14. The method of claim 11 wherein said step of bonding comprises releasably bonding said waist regions together using at least two releasable point bonds located along each side edge of said front waist region.

15. The method of claim 13 wherein said releasable point bonds bond said waist edge and said side edge of said back waist region to said side edges of said front waist region.

16. The method of claim 11 wherein said step of bonding comprises releasably bonding said side edges of said front waist region to said back waist region at a location inward of said primary fasteners.

17. The method of claim 16 wherein said side edges of said front waist region are bonded to said back waist region at a location on said front waist region inward from said side edges a distance of from about 0.2 to about 2.5 centimeters.

18. The method of claim 11 wherein said step of bonding comprises releasably bonding said waist regions together using ultrasonic bonding.

19. The method of claim 18 wherein said ultrasonic bonding comprises passing said folded absorbent article between a rotary ultrasonic horn and an anvil roll.

20. The method of claim 11 wherein said step of releasably bonding said waist regions together provides a peel strength between said waist regions of no more than about 1500 grams.

21. The method of claim 11 wherein said step of bonding releasably bonds an interior surface of said absorbent article in said back waist region to an interior surface of said absorbent article in said front waist region.

* * * * *